United States Patent
Breuninger et al.

(10) Patent No.: US 10,736,501 B2
(45) Date of Patent: Aug. 11, 2020

(54) APPARATUSES AND METHODS FOR CARRYING OUT EYE-RELATED MEASUREMENTS

(71) Applicant: Carl Zeiss Vision International GmbH, Aalen (DE)

(72) Inventors: Tobias Breuninger, Herbrechtingen (DE); Markus Seesselberg, Aalen (DE); Matthias Kubitza, Aalen (DE); Frank Widulle, Neu-Ulm (DE)

(73) Assignee: Carl Zeiss Vision International GmbH, Aalen (DE)

( * ) Notice: Subject to any disclaimer, the term of this patent is extended or adjusted under 35 U.S.C. 154(b) by 177 days.

(21) Appl. No.: 16/057,556

(22) Filed: Aug. 7, 2018

(65) Prior Publication Data

US 2019/0046027 A1 Feb. 14, 2019

(30) Foreign Application Priority Data

Aug. 14, 2017 (EP) .................................... 17186214

(51) Int. Cl.
*A61B 3/10* (2006.01)
*A61B 3/00* (2006.01)
*G02B 5/32* (2006.01)

(52) U.S. Cl.
CPC .......... *A61B 3/0091* (2013.01); *A61B 3/0083* (2013.01); *G02B 5/32* (2013.01); *A61B 3/10* (2013.01)

(58) Field of Classification Search
CPC ..... A61B 3/0025; A61B 3/103; A61B 3/1015; A61B 3/14; A61B 3/10

USPC ........................................................ 351/205
See application file for complete search history.

(56) References Cited

U.S. PATENT DOCUMENTS

| 7,384,144 B2 | 6/2008 | Ross-Messemer et al. |
| 2008/0212030 A1* | 9/2008 | Bentley .................. A61B 3/135 351/212 |
| 2008/0284979 A1* | 11/2008 | Yee ...................... A61B 3/0091 351/209 |

(Continued)

FOREIGN PATENT DOCUMENTS

| DE | 10 2015 101 687 A1 | 8/2016 |
| EP | 3 355 100 A1 | 8/2018 |

(Continued)

OTHER PUBLICATIONS

"Ophthalmic optics—Spectacle lenses—Vocabulary" (ISO 13666:2012); German and English version EN ISO 13666:2012, Oct. 2013.

(Continued)

*Primary Examiner* — Mohammed A Hasan
(74) *Attorney, Agent, or Firm* — Thrive IP®; Georg M. Hasselmann

(57) ABSTRACT

An apparatus for carrying out an eye-related measurement on a person includes a device for generating a fixation target with a holographic element. To generate the fixation target, the holographic element is illuminated by a light source. As a result of the illumination, the fixation target arises as a virtual holographic object. The eye-related measurement is conducted on an eye or the eyes of the person fixating the fixation target. Information is conveyed to the person by switching between different fixation targets.

20 Claims, 3 Drawing Sheets

(56) References Cited

U.S. PATENT DOCUMENTS

2013/0201446 A1    8/2013   Hall et al.
2018/0024361 A1    1/2018   Erler et al.

FOREIGN PATENT DOCUMENTS

| EP | 3 355 102 A1 | 8/2018 |
| EP | 3 413 122 A1 | 12/2018 |
| WO | 2005/069063 A1 | 7/2005 |

OTHER PUBLICATIONS

"Products & Services from Zeiss Vision Care," available at https://www.zeiss.com/vision-care/en_us/products.html, last accessed Jul. 31, 2018.

"3D Video measurement," Rodenstock, available at https://www.rodenstock.us/us/en/lenses/rodenstock-technologies/3d-video-measurement.html, last accessed Jul. 31, 2018.

"Computer-generated holography," Wikipedia article, available at https://en.wikipedia.org/wiki/Computer-generated_holography, last accessed Jul. 31, 2018.

"Holography," Wikipedia article, available at https://en.wikipedia.org/wiki/Holography, last accessed Jul. 31, 2018.

"Optical coherence tomography," Wikipedia article, available at https://en.wikipedia.org/wiki/Optical_coherence_tomography, last accessed Jul. 31, 2018.

"Visual field test," Wikipedia article, available at https://en.wikipedia.org/wiki/Visual_field_test, last accessed Jul. 31, 2018.

\* cited by examiner

APPARATUSES AND METHODS FOR CARRYING OUT EYE-RELATED MEASUREMENTS

CROSS REFERENCE TO RELATED APPLICATIONS

This application claims priority to European patent application EP 17 186 214.7 filed Aug. 14, 2017, which is hereby incorporated by reference in its entirety.

TECHNICAL FIELD

The present application relates to apparatuses and methods for carrying out eye-related measurements.

BACKGROUND

Eye-related measurements should be understood generally to mean measurements which determine properties of a person's eyes in isolation or measure some other object, in particular a spectacle lens, vis a vis a person's eyes. One example of an apparatus for measuring properties of the eyes themselves is a refractometer for objective refraction measurement, which determines the refraction of eyes at a position to be examined and outputs it usually in the form of sphere, cylinder and axis, as defined in DIN ISO 13666: 2012. Another example is a perimeter used to determine a person's field of view (cf. "Perimetry" in the Wikipedia Article "Visual field test," last accessed Jul. 31, 2018). A further example is an apparatus for generating sectional images of the anterior chamber or the retina of an eye, for example by means of optical coherence tomography (OCT); see Wikipedia article "Optical Coherence Tomography," last accessed Jul. 31, 2018. Further examples include apparatuses for biometry of the eye, which allow the selection of a patient-specific intraocular lens before a cataract operation, i.e., the selection of a lens to be inserted into the eye. An apparatus of this type is sold by the Carl Zeiss® Group under the designation IOL Master®. By means of such eye-related measurements that determine properties of the eye itself, measurement data (e.g., the refraction mentioned above) describing a state of the eye are thus obtained. On the basis of the measurement data, a physician or optician can then make a diagnosis by checking whether the measurement data indicate a syndrome. In the case of refraction, the diagnosis can then amount e.g., to short-sightedness or long-sightedness. This establishment of the diagnosis is thus a further procedure after the provision of the measurement data by the eye-related measurement.

One example of an apparatus that measures a spectacle lens relative to an eye for the purpose of positioning the spectacle lens is a so-called centring apparatus. Centring apparatuses are described in WO 2005/069063 A or in European Patent Applications Nos. EP 3 355 102 A1 and EP 3 355 100 A1. Centring apparatuses determine so-called centring parameters that are used by an optician for correct seating by grinding and adaptation of the spectacle lens, as explained in greater detail in these citations.

An overview of various apparatuses for refraction and centring measurement is also given by the web page www.zeiss.com/vision-care/en_us/products.html, last accessed Jul. 31, 2018. The related art discloses a wealth of further examples for the apparatuses mentioned above. Therefore, the latter will not be explained in any greater detail here.

In the case of such apparatuses, for measurement purposes it is often necessary for the person who is to be examined to adopt a specific viewing direction. By way of example, in centring measurements it is often assumed that the person has directed the gaze horizontally substantially into infinity.

To ensure that the person adopts a viewing direction required for the respective measurement, a fixation target is provided. In the context of the present application, a fixation target is understood to mean a real or virtual object or image at which the person is supposed to direct his/her gaze during the respective measurement. In this case, the object or image is virtual if it is not an actual image or object, but rather for example a spatially projected image or a mirror image.

Many apparatuses, e.g., the apparatus for 3D video measurement as shown at www.rodenstock.us/us/en/lenses/rodenstock-technologies/3d-video-measurement.html, last accessed Jul. 31, 2018, operate such that the person to be examined fixates an object, the mirror image of the person himself/herself, or a light-emitting diode fitted to the apparatus, from a relatively short distance, e.g., 1 m. A video camera then records images of the person while the latter views the fixation target thus formed. What is disadvantageous about that is that if the person takes up his/her gaze at the fixation target, the eyes adopt a so-called convergence position, i.e., are not directed into infinity. Instead, the viewing direction of both eyes extends towards the point of the fixation target, which is situated relatively close to the person (for example at the abovementioned distance of 1 m). The purely geometric convergence resulting from the position of the eyes and of the fixation target can be compensated for computationally in this case. As explained in U.S. Pat. No. 7,384,144 B2, however, this geometric convergence does not necessarily correspond to the actual convergence of the pair of eyes, that is to say that the actual position of the eyes when viewing the fixation target can deviate from the position determined from purely geometric considerations. This can in turn lead to inaccuracies during the measurement.

Therefore, U.S. Pat. No. 7,384,144 B2 proposes an apparatus for generating a fixation target, in which a speckle pattern projected into infinity is generated by means of a laser light source through a diffractive element. For this purpose, in the case of the apparatus in U.S. Pat. No. 7,384,144 B2, the laser light is projected onto a screen via a diffraction element to form a speckle pattern on the screen, and the pattern is then projected into infinity by an optical system. By way of example, the optical system can realize a magnifying glass imaging by means of a lens or lens group. In this case, a diffractive element is an element that works on the basis of light diffraction, in contrast to refractive elements such as lenses, which work on the basis of light refraction. The speckle pattern can be superimposed with an additional pattern, for example a cruciform pattern, as likewise explained in U.S. Pat. No. 7,384,144 B2.

By virtue of the speckle pattern being projected into infinity, the person basically adopts a viewing direction for which the gaze is directed into infinity. Therefore, there is no need to carry out any compensation on account of a convergence of the eyes to a comparatively closely situated point.

Nevertheless, the fixation target in U.S. Pat. No. 7,384,144 B2 still has disadvantages. Firstly, there are persons who, on account of the subjective proximity of the apparatus, exhibit a type of residual convergence, that is to say that the eyes do not exactly adapt to the viewing direction of infinity.

In addition, in the case of the apparatus in accordance with the related art, the image is fixated by both eyes (binocular vision), wherein the typical distance between the eyes is approximately 64 mm. Therefore, the optical system that generates the fixation target on the basis of the laser light is used outside its optical axis. Here, in the case of a rotationally symmetrical optical system, the optical axis is the axis of symmetry of the system and passes in particular through centers of curvature of curved surfaces. Optical systems have imaging aberrations such as spherical aberration or distortion, which prove to be more severe the further away from the optical axis. The imaging aberrations can be reduced by various measures, for example by the use of aspherical lenses, but this increases the costs.

Moreover, the apparatus in accordance with U.S. Pat. No. 7,384,144 B2 is relatively large. Since a traditional optical system comprising refractive elements, in particular lenses, is used within this apparatus, a specific distance is maintained between the refractive elements used and a screen onto which the laser light is projected as a speckle pattern. The distance corresponds approximately to the focal length of the lens. The shorter the focal length of the system, the greater the extent to which imaging aberrations become visible. On the other hand, larger focal lengths increase the structural space required.

Finally, the apparatus in accordance with U.S. Pat. No. 7,384,144 B2 is comparatively expensive. In the case of the apparatus in U.S. Pat. No. 7,384,144 B2 for generating the fixation target use is made of at least one laser, a diffractive element for generating a pattern to be projected (in particular a speckle pattern), a screen, and an imaging optical unit, typically consisting of one or more lenses. Each of these components contribute to the financial outlay.

US 2013/0201446 A1 discloses a hologram that encodes one or more holographic images. The holographic images can be used as eye charts or for eye training. In this case, the holographic images can be generated substantially at infinity or at a finite distance. Switching between the holographic images in the case of a plurality of holographic images is not explained in this case. Moreover, the use of such holographic images as a fixation target is mentioned.

SUMMARY

It is an object of the disclosure to provide an apparatus and a method for carrying out eye-related measurement comprising a device for generating a fixation target in which simple switching between different fixation targets is possible.

According to an exemplary embodiment, an apparatus for carrying out an eye-related measurement is provided which comprises a device for generating a fixation target and also a device for carrying out the eye-related measurement when a person looks at the fixation target. The device for generating the fixation target comprises a holographic element. The apparatus further comprises an illumination device for illuminating the holographic element.

This apparatus forms the starting point for the following aspects according to exemplary embodiments:

In accordance with an aspect of the apparatus, the illumination device is configured to selectively illuminate the holographic element for generating a first fixation target and a second fixation target, wherein the first fixation target differs from the second fixation target with regard to position and/or color and/or shape of the first fixation target.

In accordance with another aspect of the apparatus, the illumination device comprises a first light source having a first light wavelength and a second light source having a second light wavelength, which differs from a first light wavelength, wherein the holographic element is configured to generate the fixation target with a color corresponding to the first light wavelength upon illumination by the first light source and the fixation target with a color corresponding to the second light wavelength upon illumination by the second light source.

In accordance with yet another aspect of the apparatus, the illumination device is configured to illuminate the holographic element selectively to a first illumination type or a second illumination type, wherein the first illumination type differs from the second illumination type with regard to an illumination angle and/or a wavelength and/or an illumination location, i) wherein the holographic element is configured to generate the fixation target with a first shape upon illumination with the first illumination type, and is configured to generate the fixation target with a second shape upon illumination with the second illumination type, the second shape differing from the first shape.

In accordance with another aspect of the apparatus, the illumination device is configured to illuminate the holographic element selectively to a first illumination type or a second illumination type, wherein the first illumination type differs from the second illumination type with regard to an illumination angle and/or with regard to a wavelength and/or with regard to an illumination location, wherein the holographic element is configured to generate the fixation target upon illumination with the first illumination type and to generate a further fixation target at a different position from the fixation target upon illumination with the second illumination type.

Compared with US 2013/0201446 A1, these aspects enable simple switching between fixation targets of different shapes, colors and/or positions. This will be explained in even greater detail below.

The device for carrying out the eye-related measurement can be any device known to the skilled artisan per se, for example, a centring device, a refractometer, a perimeter, a device for generating sectional images of the anterior chamber or of the retina, or a device for biometry of the eye, such as have been explained in the introduction. Since, as explained in the introduction, such devices are known per se in many variants and the present invention relates in particular to the configuration of the device for generating the fixation target, the device for carrying out the eye-related measurement itself is not explained in any greater detail here.

If the device for generating the fixation target comprises a holographic element and an illumination device, then the illumination device can comprise one or more light sources to illuminate the holographic element. In particular, a laser light source such as a laser diode can serve as light source, wherein other types of light sources are also usable for example in the case of white light holograms.

A holographic element is a component that comprises one or more holograms. In this case, a hologram is a type of image which, in contrast to a normal photograph, records not just intensity of incident light, but rather intensity and phase. In this case, the image recording takes place with the aid of interference, for which purpose coherent light, generally a laser beam, is used, which is expanded by means of diverging lenses, for example. In this case, on a light-sensitive material, a reference beam is brought to interference with an illumination beam that illuminates an object recorded on the hologram. The light-sensitive material thus exposed, after a development step, can either serve directly as a hologram or be used for producing corresponding holograms by replication methods. A large number of holograms of identical type can be produced cost-effectively in this way. If the hologram is then illuminated with corresponding coherent light from that direction from which the reference beam impinged on the light-sensitive material during image recording, the object appears at the location at which the object was situated during image recording. In another type of holograms, also referred to as a holographic ground-glass screen, two light beams are brought to interference, wherein in this case no object is present in the illumination beam, rather the illumination beam emanates from a point. In this regard, a holographic ground-glass screen can be produced in which the hologram can then be scanned from the direction of the reference wave by a laser and an object then arises for instance at the location of the point of the illumination beam. The shape of the object is defined by the laser light being switched on and off during scanning. This principle is also used for example for data projection, as described in US 2018/0024361 A1.

Further details concerning the production of holograms can be found for example in the Wikipedia article "Holography," last accessed Jul. 31, 2018. As explained in the article mentioned above, holograms can be classified according to various properties, in particular as volume, surface holograms, amplitude holograms, or phase holograms. In the case of volume holograms, the holographic information (i.e., an interference pattern) is also stored in a thickness direction of the hologram, whereas in the case of surface holograms the interference is recorded substantially in a plane of light-sensitive material. Moreover, a distinction can be drawn between white light holograms and holograms which cannot be reconstructed under white light, and also true-color holograms, wherein only volume holograms can be white light holograms. The hologram can be configured as a transmission hologram or as a reflection hologram. In the case of a transmission hologram, the hologram is illuminated from one side and viewed from the other side. In this case, a virtual holographic object arises on the same side of the hologram from which illumination is also affected. In this case, the hologram is thus arranged between the light source of the illumination device and the observer. In the case of a reflection hologram, the illumination by the light source is affected from the same side from which the observer also views the hologram. These types of hologram are likewise explained in the above Wikipedia article "Holography". In principle, any type of hologram can be used as a hologram of the holographic element, with volume holograms being typical. The latter can be produced cost-effectively and can also contain a plurality of holograms stacked one above another in the thickness direction, i.e., a direction perpendicular to the surface.

If the holographic element is illuminated with the illumination device or by an extraneous light source, the holographic element generates the fixation target as a holographic image in accordance with the above explanations. In the context of the present application, the holographic image is also referred to as a virtual holographic object. Virtual because it is not a real object, but rather just an image of an object used during the production of the hologram as explained in the introduction or—in the case of a holographic ground-glass screen as holographic element—as an image of a pattern illuminated on the holographic element by means of the light source.

As a result of the illumination by the light source, the hologram then generates the fixation target at a location which depends on the design during the recording of the hologram as explained above, i.e., at the location at which the object was positioned during recording. A realization as a holographic ground-glass screen as explained above is likewise possible. In this case, it is possible to realize the shape of a projected object by corresponding scanning and driving of the light source, as explained in US 2018/0024361 A1 for a different application, namely data projection.

The use of a holographic element for generating the fixation target has the following advantages over the prior art such as in U.S. Pat. No. 7,384,144 B2:

By means of the holographic element, a very good optical quality can be achieved in conjunction with low production costs. The virtual image of the object that is generated by the holographic element can be viewed well from different directions. As a result, such a fixation target is very well suited especially to the binocular use, i.e., for viewing with both eyes. Moreover, the holographic fixation target thus generated is subjectively perceived by the person as a real fixation object floating in space. The disadvantage of a possible residual convergence is thus eliminated. Furthermore, the hologram can be illuminated by a small laser light source at a relatively steep angle (if, during production, the reference beam is directed onto the light-sensitive material at a corresponding steep angle, as described above). In this regard, a smaller structural space than in the related art can be realized. Finally, compared with the related art explained above, the diffractive element, the screen and the optical system can be replaced by the holographic element. More expedient production than in the case of the device in U.S. Pat. No. 7,384,144 B2 is possible as a result.

Typically, the holographic element is configured to generate the fixation target upon illumination at a distance of at least 4 m, more typically at least 8 m, from the holographic element. At such distances the convergence of the eyes when viewing the fixation target corresponds at least approximately to a gaze into infinity. Such distances can be realized in a simple manner by virtue of the fact that during illuminating an object that is illuminated by the illumination beam is arranged at a corresponding distance from a light-sensitive material used in the production of the hologram.

In this case, the fixation target typically has a region to be fixated, i.e., a region that the person is intended to fixate during an eye-related measurement, having an extent which corresponds to a viewing angle of <1°, particularly <0.5°, as viewed from the holographic element. This angle substantially corresponds to the arc tangent of the extent of the region to be fixated of the fixation target divided by the distance between the fixation target and the holographic element. In this case, the extent should be understood to be perpendicular to the distance. Given a distance of 8 m, this results, e.g., in an extent of approximately less than 14 cm, typically less than approximately 7 cm. A defined viewing direction of the eyes can be achieved with such a small extent. In the case of larger extents, inaccuracies could occur here because the person could view different parts of an extensive fixation target, which would lead to corresponding different eye positions. In this case, the region to be fixated is a region that is distinguishable from other regions of the fixation target, such that the person can be given the instruction to fixate the distinguishable region. In this case, the entire fixation target can have a relatively large extent (e.g., corresponding to a viewing angle of 20° or more), wherein this angle substantially corresponds to the arc tangent of the dimension of the entire fixation target divided by the distance between the fixation target and the holographic element, to make it easier for persons with greatly defective vision to recognize the fixation target in the first place.

Holograms, in particular volume holograms, are wavelength-selective and angle-selective.

Wavelength-selective means that the hologram actually generates an image only upon illumination with that wavelength with which it was illuminated (within a certain tolerance range). Angle-selective means that the hologram generates an image only upon illumination at that angle (once again with a certain tolerance) at which it was illuminated with the reference beam. These properties can be utilized in the first to fourth aspects of the present application in order to equip the device according to some embodiments for generating the fixation target with additional features and, by comparison with US 2013/0201446 A1, to achieve simple switching between different fixation targets having different colors, shapes and/or positions.

In exemplary embodiments as mentioned as mentioned above, the device can be configured to generate the fixation target in different colors. In this case, the holographic element comprises two or more holograms which were generated in each case with coherent light of a different wavelength. In the case of volume holograms, the two or more holograms can be applied one above another in a thickness direction of the hologram. In this case, the thickness direction is a direction perpendicular to a surface of the volume hologram, in particular a surface that is illuminated for the purpose of generating the fixation target. However, provision alongside one another or in separate holograms is likewise possible.

Accordingly, the illumination device then comprises a plurality of light sources of the corresponding different wavelengths (including the light source already mentioned) for generating fixation targets of different colors.

By means of the different colors, in one exemplary embodiment, a person who is being examined by the apparatus can be given information. In this case, information should be understood to mean indications, instructions, and/or feedback to the person, in addition to the mere presence of a fixation target, i.e., in addition to the fact that a fixation target is provided to which the person is supposed to direct his/her gaze.

By way of example, in the case of the centring apparatus described in European Patent Applications Nos. EP 3 355 102 A1 and EP 3 355 100 A1, the position of the person's head can be captured by means of cameras and can be compared with a setpoint position for the centring measurement. By way of the color of the fixation target, the person can then be given, as information, feedback as to whether the position of the head is correct, e.g., on the basis of traffic light colors red, amber, and green.

In the same way as different colors, alternatively or additionally different shapes can also selectively be represented, as mentioned in the case of the first or third aspect. For this purpose, the two or more holograms are illuminated by means of objects having such different shapes, or the holographic ground-glass screen mentioned above is used. The different shapes can be arrows, for example, which indicate to the person as information the direction in which the person ought to move his/her head to achieve a setpoint position for the measurement. By virtue of the fact that the fixation target itself assumes different colors or shapes, the person can obtain the information communicated by the colors or shapes without averting the gaze from the fixation target.

Additionally, or in some exemplary embodiments alternatively, the device for generating the fixation target can be configured to generate one (or more) further fixation targets at different positions from the fixation target. For this purpose, two or more holograms can be used, as in the procedure for different colors or shapes. The holograms can be encoded simultaneously, for example in different layers of the volume hologram, or be configured as a corresponding computer-generated hologram (CGH), see the Wikipedia article "Computer generated holography", last accessed Jul. 31, 2018.

They can be "switched" by different light sources, for example with different light wavelengths (light wavelength selectivity of holograms) or by illuminations at different angles (angle selectivity of holograms). The holograms can also be arranged in a manner spatially separated in the holographic device and be illuminated separately in this way, such that different illumination locations are used. In this regard, by means of different illumination types (different with regard to light wavelength, illumination angle and/or illumination location), it is possible to choose and switch in a simple manner between different colors, shapes, and/or positions for the fixation target.

Besides different light sources for different illumination types, different illumination angles or illumination locations can also be realized with a single light source, which is then directed at the holographic element by means of movable mirrors at different angles and/or at different locations.

While the fixation target, as explained above, can be generatable at a great distance, >4 m or >8 m, and thus serves as a fixation target for a gaze into the distance (approximately into infinity), a further fixation target can serve as a so-called near gaze target, i.e., be arranged at a short distance (for example <1 m, or <50 cm, in particular approximately 30 cm), that is to say in the range of a typical reading distance. From measurements when the person then directs the gaze to the near gaze target, it is possible to deduce an eye position during reading, which can be used for the so-called near centring. Moreover, the fulcrum of the eye can be determined from such measurements. The near centring serves for centring in the case of progressive lenses, which have a near portion for near vision, in particular reading. Using the near gaze target generated by the apparatus according to some embodiments, the near centring and the determination of the fulcrum of the eye can be carried out in a manner known per se, for example as described in the European Patent Application EP 3 413 122 A1. Moreover, by means of different positions the person can also be given information, e.g., as to how his/her head is to be positioned.

As a result, in a simple manner and with little structural space, it is possible to provide different fixation targets for different purposes.

As an alternative to the above-described optional generation of a fixation target for the gaze into the distance and a further fixation target as a near gaze target depending on the illumination type, it is also possible to generate a single fixation target having a first part, which is at a distance of more than 4 m from the holographic element and can thus serve for fixation for the gaze into the distance, and a second part, which is at a distance of less than 1 m from the holographic element and can thus serve as a near gaze target. In this case, the virtual holographic object has the first part and the second part and thus a corresponding spatial extent. This variant is less typical, however, since both parts are simultaneously visible to the person to be examined and it can therefore happen that the person directs his/her gaze at the "wrong" part for a respective eye-related measurement (e.g., at the second part for a distance centring or the first part for the near centring) or the person's gaze shifts back and forth between the first and second parts.

The device for generating the fixation target can further comprise a transparent protective covering, for example a glass plate, to protect the device against dirt or environmental influences.

In accordance with an aspect of the disclosure, a method is provided, comprising:

illuminating a holographic element for generating a fixation target; and carrying out an eye-related measurement while a person looks at the fixation target. This method forms the basis for further aspects of some embodiments corresponding to the above-discussed aspects of the apparatus, by means of which simple switching between different colors, shapes, and/or positions is achievable.

As explained for the above apparatus, a fixation target can be generated in a simple manner with the holographic element. The eye-related measurement can in turn be any type of measurement in which a viewing direction for the person is intended to be defined by the fixation target, such as the above-explained centring measurements, refraction measurements, biometry measurements, and the like.

The abovementioned exemplary embodiments of the apparatus can correspondingly also be applied to the method, with the corresponding advantages. In this regard, the holographic element can selectively be illuminated for generating fixation targets in different colors and/or shapes, or selectively be illuminated for generating fixation targets at different locations (for example as near gaze target and distance gaze target). For this purpose, the illumination can be varied with regard to light wavelength, illumination angle, and/or illumination location, as described. The fixation target can be generated with an extent of a region to be fixated such that a viewing angle of <1°, typically <0.5°, results for the person.

BRIEF DESCRIPTION OF THE DRAWINGS

The disclosure will now be described with reference to the drawings wherein:

FIG. 1 shows an exemplary embodiment of a centring apparatus in accordance with the disclosure. The apparatus in FIG. 1 comprises a semicircular arrangement of cameras 12, which is secured on a column 11. A person then positions himself/herself in such a way that a head 13 of the person, as shown in FIG. 1, is positioned in the semicircular camera arrangement 12 and can be recorded from different directions.

Figure 1:
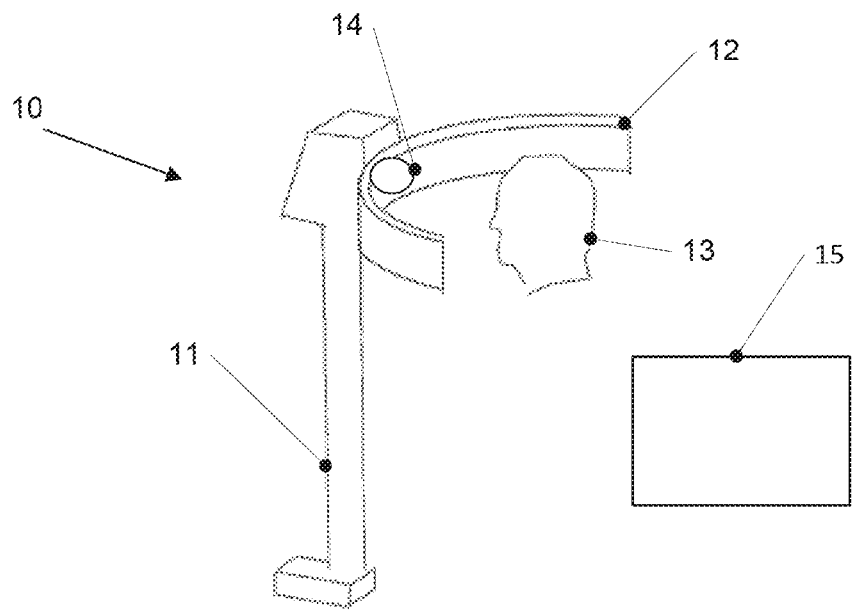
FIG. 1 shows an apparatus for centring measurement in accordance with an exemplary embodiment.

The apparatus 10 in FIG. 1 further comprises a device 14 for generating a fixation target to which the person is supposed to direct his/her gaze during image recording. In this case, the device 14 comprises a holographic element to generate the fixation target. Exemplary embodiments of such devices for generating a fixation target will be explained in greater detail below with reference to FIGS. 2 to 4.

The recorded images are then evaluated by a computing device 15, for example to determine centring parameters during the centring measurement. Apart from the provision of the device 14 comprising a holographic element, the apparatus in FIG. 1 corresponds to the apparatuses described in European Patent Applications Nos. EP 3 355 102 A1 and EP 3 355 100 A1 and will therefore not be explained any further. In particular, the apparatus 10 represents only one possible exemplary embodiment of an apparatus for carrying out an eye-related measurement in which the device 14 for generating the fixation target can be used, as already explained initially.

Figure 2:
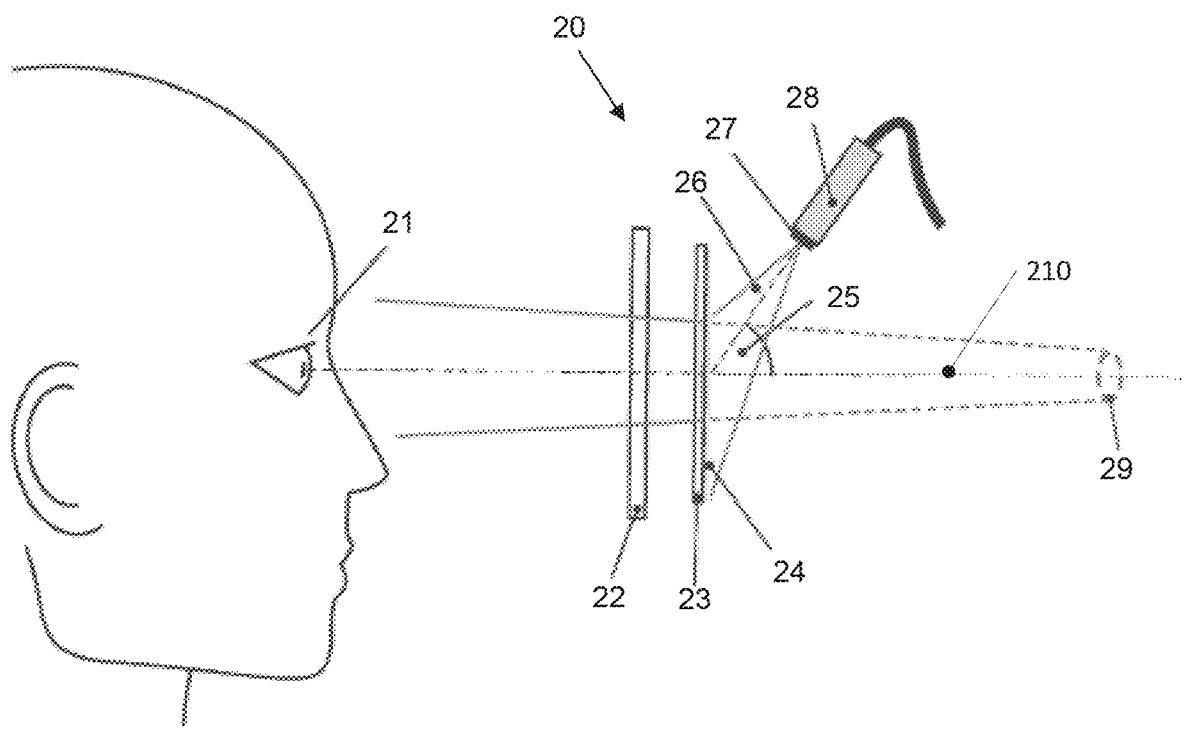
FIG. 2 shows an exemplary embodiment of a device for generating a fixation target with a transmission hologram.

FIG. 2 shows an exemplary embodiment of a device 20 for generating a fixation target 29 in accordance with the disclosure. The device 20 can be used for example as the device 14 in FIG. 1.

The device 20 in FIG. 2 comprises a glass substrate 23 with a holographic layer 24, i.e., a layer in which one or more holograms are arranged. Furthermore, the device 20 in FIG. 2 comprises a laser light source 28. In the case of the exemplary embodiment in FIG. 2, the laser light source 28 is a laser diode. The laser light source 28 generates a laser beam that is expanded by an optical unit 27, whereas 26 denotes a center axis of the laser beam expanded by optical unit 27.

The center axis 26 forms an illumination angle 25 with a line 210 that is perpendicular to the glass substrate 23. The illumination angle is chosen in accordance with an illumination angle during production of the holographic layer 24. During illumination, a virtual holographic object is then generated as a fixation target 29, which can be viewed by a person's eye 21 in accordance with the line 210, which here simultaneously indicates the viewing direction.

It should be taken into consideration that FIG. 2 is not drawn to scale, and in particular the distance between the fixation target 29 and the holographic layer 24 can be greater than appears in the drawing. Specifically, the distance can be greater than or equal to 8 m, such that the person's viewing direction substantially corresponds to a gaze into infinity.

Moreover, the device 20 also comprises a glass plate 22, which protects the device 20 against contamination and also against damage for example as a result of inadvertent touching.

The holographic layer 24 in FIG. 2 operates in transmission, which means that, in the case of FIG. 2, the laser light source 28 and the fixation target 29 are arranged on the same side of the holographic layer 24, while the eye 21 is arranged on the other side. The light from the laser light source thus passes through the holographic layer 24 (transmission) to the eye 21.

Figure 3:
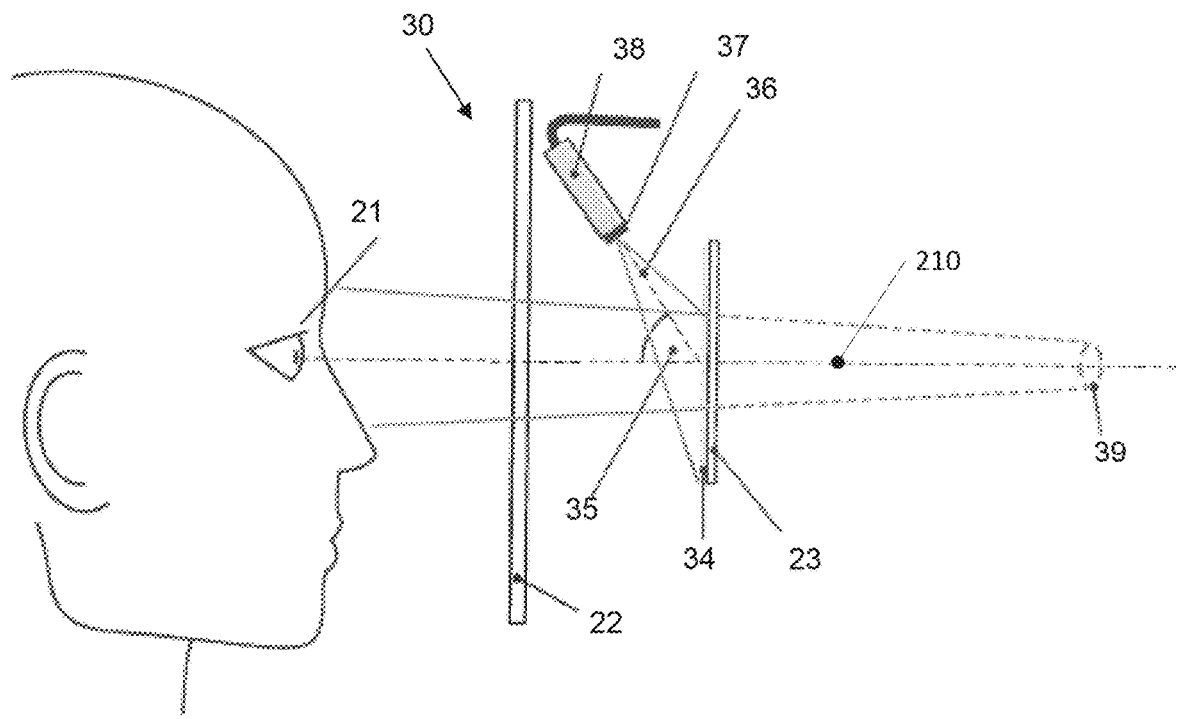
FIG. 3 shows an exemplary embodiment of a device for generating a fixation target with a reflection hologram.

By contrast, FIG. 3 shows a device 30 that operates in reflection. Elements in FIG. 3 which correspond to elements in FIG. 2 bear the same reference signs and will not be explained again. Elements in FIG. 3 which have been modified by comparison with the elements in FIG. 2 to obtain an arrangement in reflection are identified by the same reference sign increased by the number 10.

In the exemplary embodiment in FIG. 3, once again a holographic layer 34 is arranged on the glass substrate 23. A laser light source 28 generates a laser beam that is expanded by an optical unit 37. The reference sign 36 denotes a center axis of the expanded beam, which forms an angle 35 with respect to the perpendicular line 210 on the holographic layer 34. The angle 35 is once again chosen in accordance with an illumination angle during production of the hologram, as explained above.

During illumination of the holographic layer 34, a virtual holographic object is then generated as a fixation target 39, which, like the fixation target 29 in FIG. 2, can be viewed by the person in accordance with a viewing direction along the line 210. Like FIG. 2, FIG. 3 is not to scale either, and the fixation target 39 is typically at a distance of 8 m or more from the holographic layer 34.

The holographic layer 34 in FIG. 3 operates as a reflection hologram, as already mentioned, that is to say that the light source 38 illuminates the holographic layer 34 from a side from which the holographic layer 34 is also viewed by the eye 21, as illustrated, and the fixation target 39 arises on the other side of the holographic layer 34. Therefore, in this case, the light from the laser light source 28 is reflected from the holographic layer 34 to the eye 21.

Figure 4:
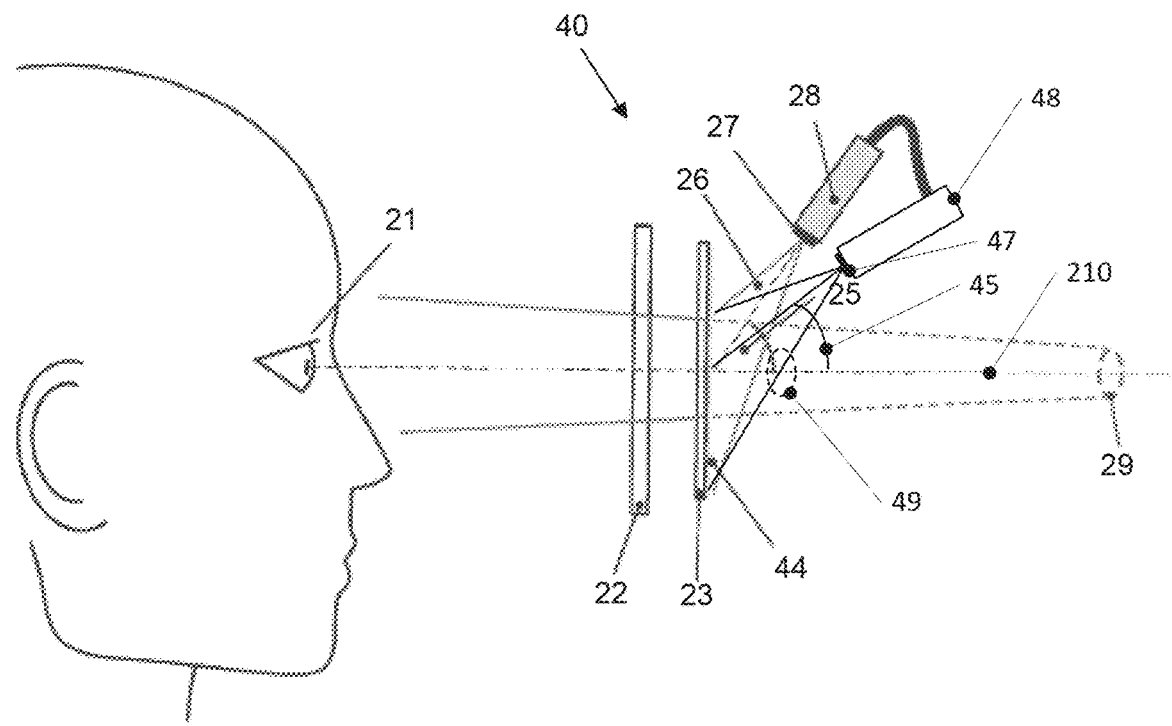
FIG. 4 shows an exemplary embodiment of a device for generating a fixation target selectively at different locations.

FIG. 4 shows a device 40 for selectively generating two fixation targets. In this case, the apparatus in FIG. 4 is based on the apparatus in FIG. 2, and identical elements bear the same reference signs. In particular, in the exemplary embodiment in FIG. 4, the fixation target 29 is generated by illumination of a holographic layer 44 by the laser light source 28 at the angle 25.

Moreover, in the exemplary embodiment in FIG. 4, provision is made for a further laser light source 48 with a corresponding further optical unit 47 for expanding the laser beam, which is configured to illuminate the holographic layer 44 at an angle 45 that differs from the angle 25. In the holographic layer 24 two holograms are stored, one for the angle 25 and one for the angle 45, for example in different layers of a volume hologram. Upon illumination of the holographic layer 44 by means of the laser light source 28, as explained above, the fixation target 29 is generated as fixation target. Upon illumination of the holographic layer 44 by the laser light source 48, instead a virtual holographic object is generated as a fixation target 49, which lies nearer to the eye 21 than the fixation target 29 and can serve as a near gaze target as explained further above. By way of example, the distance between the fixation target 49 and the holographic layer 44 can be between 10 and 50 cm, for example such that the distance to the eye 21 is approximately 30 cm.

While the fixation target 49 is likewise generated on the line 210 in FIG. 4, it can also be generated away from the line 210, for example in a manner offset downwards, corresponding to a viewing direction during reading.

In a manner corresponding to that by which different fixation targets 29, 49 are generated at different locations by two lasers 28, 48 in FIG. 4, additionally or alternatively, it is also possible to selectively generate fixation targets with different colors and/or shapes as explained above, which can then also be situated at the same location.

Figure 5:
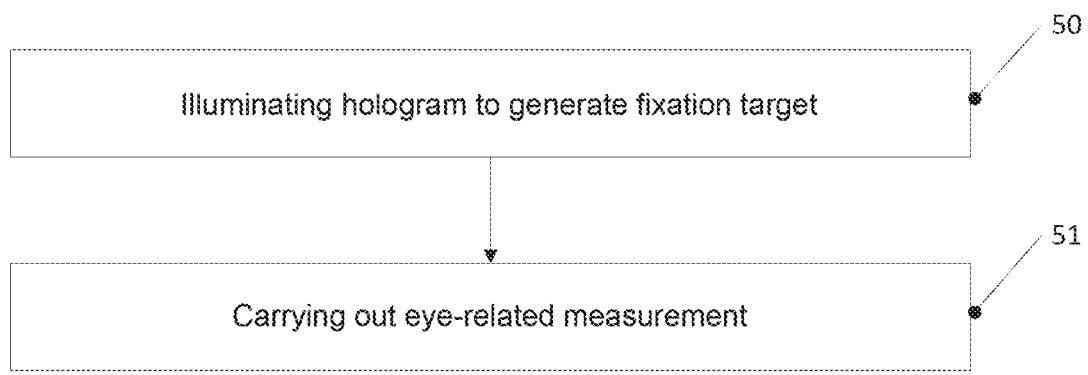
FIG. 5 shows a flow diagram for illustrating a method in accordance with an exemplary embodiment.

FIG. 5 shows a flow diagram of a method in accordance with an embodiment. Step 50 involves illuminating a hologram for generating a fixation target, for example the holographic layer 24 from FIG. 2 for generating the fixation target 29, illuminating the holographic layer 34 for generating the fixation target 39, or illuminating the holographic layer 44 for generating the fixation targets 29 or 49.

Step 51 then involves carrying out an eye-related measurement while a person looks at the fixation target. By way of example, a centring measurement by means of the centring apparatus 10 from FIG. 1 or another of the eye-related measurements mentioned in the introduction is carried out.

Figure 6:
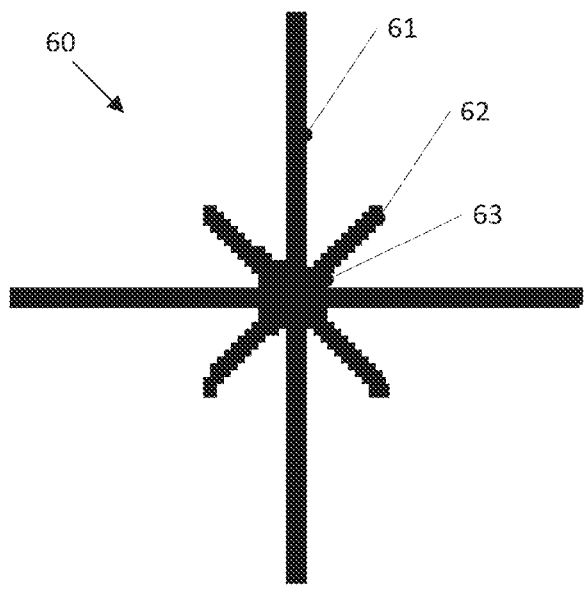
FIG. 6 shows an exemplary embodiment of a fixation target such as is generatable by an apparatus according to some exemplary embodiments.

FIG. 6 shows one example of a fixation target 60 such as is generatable by means of the apparatuses and methods explained above. In this case, the fixation target 60 can be generated as a bright fixation target (in a color corresponding to the color of the light source used) against a dark background.

The fixation target 60 comprises a larger cross 61 and a smaller cross 62, which is rotated by an angle of 45° with respect to the larger cross 61, and also a central region 63, in which bars of the crosses 61, 62 intersect. The terms "larger" and "smaller" should be understood here in relative fashion, that is to say that the larger cross 61, as illustrated, is larger than the smaller cross 62.

The central region 63 represents one example of a region to be fixated of the fixation target 60, that is to say that the person to be examined is given the instruction (by a physician, optician or else the apparatus itself) to fixate this region. In this case, as explained, the central region 63 has an extent corresponding to a viewing angle of <1°, in particular less than 0.5°. In this case, the viewing angle should be considered from the person's viewpoint and, in the case of fixation targets which are generated at a large distance such as the 8 m mentioned, corresponds approximately to a viewing angle as seen from the hologram which generates the fixation target.

By comparison therewith, the entire fixation target 60 has a larger extent in order to enable persons with greatly defective vision to recognize the fixation target. In this regard, the larger cross 61 can have an extent corresponding to a viewing angle of 20°.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. An apparatus for carrying out an eye-related measurement, the apparatus comprising:
   a generating device having a holographic element configured to generate a first fixation target and a second fixation target;
   a measuring device configured to carry out the eye-related measurement while a person looks at the first fixation target or the second fixation target; and
   an illumination device configured to illuminate the holographic element;
   wherein the illumination device is configured to selectively illuminate the holographic element to generate at least one of the first fixation target or the second fixation target, and wherein the first fixation target differs from the second fixation target in at least one of a position, a color, or a shape thereof.

2. The apparatus according to claim 1, wherein the apparatus is configured to select the first fixation target or the second fixation target for communicating to a person information in addition to a mere presence of the first fixation target, the second fixation target, or the first fixation target and the second fixation target.

3. The apparatus according to claim 2, further comprising:
a camera configured to capture a position of the person's head,
wherein the apparatus is configured to compare the position of the person's head with a target position, and
wherein the information indicates whether the person's head is positioned correctly for carrying out the eye-related measurement.

4. The apparatus according to claim 1, wherein the holographic element is configured to generate the first fixation target at a distance of at least 4 m from the holographic element.

5. The apparatus according to claim 1, wherein the holographic element is configured to generate the first fixation target as a region having a spatial extent, and
wherein an arc tangent of the spatial extent divided by a distance between the first fixation target and the holographic element is <5°.

6. The apparatus according to claim 1, wherein the illumination device comprises a first light source having a first light wavelength and a second light source having a second light wavelength, which differs from a first light wavelength, and
wherein selectively illuminating comprises selectively illuminating the holographic element with the light of the first light wavelength or the light of the second light wavelength.

7. The apparatus according to claim 1, wherein selectively illuminating comprises illuminating the holographic element selectively to a first illumination mode or a second illumination mode, and
wherein the first illumination mode differs from the second illumination mode with regard to at least one of an illumination angle, a wavelength, or an illumination location.

8. The apparatus according to claim 4, wherein the holographic element is configured to generate the first fixation target at the distance of at least 8 m, from the holographic element.

9. An apparatus for carrying out an eye-related measurement, the apparatus comprising:
a generating device having a holographic element configured to generate a first fixation target and a second fixation target;
a measuring device configured to carry out the eye-related measurement while a person looks at the first fixation target or the second fixation target; and
an illumination device configured to illuminate the holographic element;
wherein the illumination device comprises a first light source having a first light wavelength and a second light source having a second light wavelength, which differs from a first light wavelength, and
wherein the holographic element is configured to generate the first fixation target with a color corresponding to the first light wavelength upon illumination by the first light source and the second fixation target with a color corresponding to the second light wavelength upon illumination by the second light source.

10. The apparatus according to claim 9, wherein the apparatus is configured to selectively activate the first light source or the second light source to communicate information to the person.

11. The apparatus according to claim 10, further comprising:
a camera configured to capture a position of the person's head,
wherein the apparatus is configured to compare the position of the person's head with a target position, and
wherein the information indicates whether the person's head is positioned correctly for carrying out the eye-related measurement.

12. The apparatus according to claim 10, wherein the information comprises at least one of indications, instructions, or feedback to the person, in addition to a mere presence of the first fixation target, the second fixation target, or the first fixation target and the second fixation target.

13. An apparatus for carrying out an eye-related measurement, the apparatus comprising:
a generating device having a holographic element configured to generate a first fixation target and a second fixation target;
a measuring device configured to carry out the eye-related measurement while a person looks at the first fixation target or the second fixation target; and
an illumination device configured to illuminate the holographic element;
wherein the illumination device is configured to illuminate the holographic element selectively in a first illumination mode or a second illumination mode,
wherein the first illumination mode differs from the second illumination mode with regard to at least one of an illumination angle, a wavelength, or an illumination location thereof, and
wherein the holographic element is configured to generate the first fixation target with a first shape upon illumination in the first illumination mode, and to generate the second fixation target with a second shape upon illumination in the second illumination mode, the second shape differing from the first shape.

14. The apparatus according to claim 13, wherein the apparatus is configured to selectively activate the first illumination mode or the second illumination mode to communicate information to the person.

15. The apparatus according to claim 14, further comprising:
a camera configured to capture a position of the person's head,
wherein the apparatus is configured to compare the position of the person's head with a target position, and
wherein the information indicates whether the person's head is positioned correctly for carrying out the eye-related measurement.

16. The apparatus according to claim 14, wherein the information comprises at least one of indications, instructions, or feedback to the person, in addition to a mere presence of the first fixation target, the second fixation target, or the first fixation target and the second fixation target.

17. An apparatus for carrying out an eye-related measurement, the apparatus comprising:

a generating device having a holographic element configured to generate a first fixation target and a second fixation target;

a measuring device configured to carry out the eye-related measurement while a person looks at the first fixation target or the second fixation target; and an illumination device configured to illuminate the holographic element;

wherein the illumination device is configured to illuminate the holographic element selectively in a first illumination mode or a second illumination mode, wherein the first illumination mode differs from the second illumination mode with regard to at least one of an illumination angle, a wavelength, or an illumination location, and wherein the holographic element is configured to generate the first fixation target upon illumination in the first illumination mode and to generate the second fixation target at a different position from the first fixation target upon illumination in the second illumination mode.

18. The apparatus according to claim 17, wherein the apparatus is configured to selectively activate the first illumination mode or the second illumination mode to communicate information to the person.

19. The apparatus according to claim 18, further comprising:

a camera configured to capture a position of the person's head, wherein the apparatus is configured to compare the position of the person's head with a target position, and wherein the information indicates whether the person's head is positioned correctly for carrying out the eye-related measurement.

20. The apparatus according to claim 18, wherein the information comprises at least one of indications, instructions, or feedback to the person, in addition to a mere presence of the first fixation target, the second fixation target, or the first fixation target and the second fixation target.

* * * * *